United States Patent
Rendu et al.

(10) Patent No.: US 10,962,525 B2
(45) Date of Patent: Mar. 30, 2021

(54) PROCESS FOR CHARACTERIZING A BLOOD SAMPLE

(71) Applicants: SORBONNE UNIVERSITE, Paris (FR); INSERM (Institut National de la Santé et de la Recherche Médicale), Paris (FR); CONCEPTION DE SYSTEMES ET TECHNOLOGIE MECANIQUE: CSTM, Castanet Tolosan (FR)

(72) Inventors: Francine Rendu, Paris (FR); Monique Dufilho, Paris (FR); François Dugue, Pompertuzat (FR)

(73) Assignees: SORBONNE UNIVERSITE, Paris (FR); INSERM (INSTITUT NATIONAL DE LA SANTÉ ET DE LA RECHERCHE MÉDICALE, Paris (FR); CONCEPTION DE SYSTEMES ET TECHNOLOGIE MECANIQUE: CSTM, Castanet Tolosan (FR)

( * ) Notice: Subject to any disclaimer, the term of this patent is extended or adjusted under 35 U.S.C. 154(b) by 101 days.

(21) Appl. No.: 16/347,656

(22) PCT Filed: Nov. 6, 2017

(86) PCT No.: PCT/EP2017/078372
§ 371 (c)(1),
(2) Date: May 6, 2019

(87) PCT Pub. No.: WO2018/083315
PCT Pub. Date: May 11, 2018

(65) Prior Publication Data
US 2019/0346424 A1  Nov. 14, 2019

(30) Foreign Application Priority Data
Nov. 7, 2016 (FR) ...................... 1660749

(51) Int. Cl.
*G01N 33/49* (2006.01)
*G01N 27/22* (2006.01)
*G01N 33/50* (2006.01)

(52) U.S. Cl.
CPC ......... *G01N 33/4905* (2013.01); *G01N 27/22* (2013.01); *G01N 33/49* (2013.01); *G01N 33/50* (2013.01)

(58) Field of Classification Search
CPC ...... G01N 33/00; G01N 33/48; G01N 33/483; G01N 33/487; G01N 33/49;
(Continued)

(56) References Cited

U.S. PATENT DOCUMENTS 5,023,054 A * 6/1991 Sato .................. G01N 15/0272
                                                          210/335
5,607,565 A * 3/1997 Azarnia .................. C12Q 1/00
                                                          204/401

(Continued)

FOREIGN PATENT DOCUMENTS

| EP | 2053387 A1 | 4/2009 |
| WO | 2009/053841 A2 | 4/2009 |

OTHER PUBLICATIONS

International Search Report, dated Feb. 13, 2018, from corresponding PCT application No. PCT/EP2017/078372.

*Primary Examiner* — Hoai-An D. Nguyen
(74) *Attorney, Agent, or Firm* — Nixon & Vanderhye (57) ABSTRACT

A process for characterizing a blood sample includes: insertion, into a channel with an inlet and outlet, of a solution including blood platelets, the solution being inserted via the inlet of the channel; creating a pressure difference between the inlet and the outlet to move the solution from the inlet towards the outlet of the channel; passage of the solution into a measurement zone of the channel, provided with electrodes; measurement, by the electrodes and measure- (Continued)

ment element, of an electric signal while the electrodes are covered by the solution in the channel. The progression of the solution from the inlet towards the outlet of the channel includes a progression of a front between, on the one hand, the solution extending from the front towards the inlet of the channel and, on the other hand, a gas extending from the front towards the outlet of the channel.

20 Claims, 3 Drawing Sheets

(58) Field of Classification Search
CPC .. G01N 33/4905; G01N 33/491; G01N 33/50; G01N 33/5002; G01N 27/00; G01N 27/02; G01N 27/22; G01N 27/26; G01N 27/28; G01N 27/30; G01N 27/327; G01N 27/3271
USPC .................................. 324/600, 649, 658, 663
See application file for complete search history.

(56) References Cited

U.S. PATENT DOCUMENTS

| 8,673,215 | B2 | 3/2014 | Rendu et al. |
| 2003/0113833 | A1* | 6/2003 | Oka ................... G01N 33/48728 435/29 |
| 2007/0202560 | A1* | 8/2007 | Kikuchi ............ B01L 3/502707 435/14 |
| 2009/0218238 | A1* | 9/2009 | Dasgupta ............... G01N 30/64 205/789 |
| 2010/0330605 | A1 | 12/2010 | Rendu et al. |
| 2012/0247964 | A1* | 10/2012 | Lee .......................... C25D 1/10 205/70 |
| 2013/0083311 | A1 | 4/2013 | Li et al. |
| 2015/0020613 | A1* | 1/2015 | Niiyama ................ G01N 33/49 73/863.21 |
| 2017/0296112 | A1* | 10/2017 | Lim ..................... A61B 5/0059 |
| 2019/0079050 | A1* | 3/2019 | Zaitsu ..................... H01J 49/26 |

* cited by examiner

PROCESS FOR CHARACTERIZING A BLOOD SAMPLE

TECHNICAL FIELD

The present invention relates to a process for characterizing a blood sample.

Such a device makes it possible, for example, for a user to measure and/or characterize the aggregation of platelets in a blood sample.

STATE OF THE ART

A process for characterizing a blood sample using a device as described in the document WO 2009/053841 is known.

This document proposes as a process, pre-filling a capillary tube with water, then introducing a blood sample into the capillary tube. The passage of the front separating the two liquids produces a variation in capacitance between two measurement electrodes, which is measured and makes it possible to detect and/or characterize the state of activation of the platelets in the blood sample.

However, such a process poses two technical problems concerned with:
  possible improvement to the reproducibility of the measurements and/or
  better discrimination between different blood samples,
  improvement in the reproduction of the physiopathological conditions.

The aim of the present invention is to solve at least one of these problems.

DISCLOSURE OF THE INVENTION

This objective is achieved with a process for characterizing a blood sample, comprising:
  introducing a solution comprising blood platelets into a channel, said channel comprising an inlet and an outlet, the solution being introduced through the inlet of the channel,
  creating a pressure difference between the inlet and the outlet of the channel, so as to move the solution forward from the inlet towards the outlet of the channel,
  passing the solution into a measurement zone of the channel equipped with electrodes,
  measuring an electrical signal using measurement means and said electrodes, while said electrodes are covered with the solution in the channel,
characterized in that the forward movement of the solution from the inlet towards the outlet of the channel comprises a forward movement of a front between:
the solution extending from the front towards the inlet of the channel on the one hand, and
a gas extending from the front towards the outlet of the channel on the other hand.

During the passage of the front through the inlet of the channel, the solution preferably has a shear rate at the internal walls of the channel greater than 10,000 $s^{-1}$.

During the forward movement of the front from the inlet towards the outlet of the channel, the solution preferably has a shear rate at the internal walls of the channel which decreases with time as the front moves forward between the solution and the gas, preferably until the front reaches the outlet of the channel.

During the passage of the front through the outlet of the channel, the solution preferably has a shear rate at the internal walls of the channel less than 1,000 $s^{-1}$.

The pressure difference between the inlet and the outlet of the channel is preferably constant during the forward movement of the solution in the channel, preferably at least until the front reaches the outlet of the channel and/or up to the measurement.

The channel preferably has a cross-sectional area that is constant from its inlet to its outlet.

The pressure difference between the inlet and the outlet of the channel is preferably created by suction on the side with the outlet of the channel.

The front preferably has a forward movement velocity in the channel which decreases with time during the forward movement of the solution in the channel, preferably until the front reaches the outlet of the channel.

The gas is preferably air.

The measurement of the electrical signal is preferably carried out when:
  the progression of the solution from the inlet towards the outlet of the channel is in a steady state, and/or
  the channel is filled with the solution from the inlet to the outlet of the channel.

Starting from the inlet of the channel, the electrodes are preferably situated in a second half of the channel. The channel is preferably serpentine-shaped with several loops. The electrodes of the measurement zone are preferably situated on the last loop of the channel (with respect to the inlet of the channel).

Based on the measurement of the electrical signal, the process according to the invention can also comprise a calculation of an item of data relating to platelet discrimination and/or coagulation.

The measurement means preferably impose an electrical current between the electrodes and measure a voltage between the electrodes while the electrical current is imposed, this electrical current preferably being constant during the measurement.

The process according to the invention can comprise an integration, over time, of the voltage measured.

The process according to the invention can comprise:
detecting the passage of the front between the electrodes and the outlet of the channel, preferably by means of photodiodes and/or
measuring a velocity of the solution in the channel, preferably by means of photodiodes, and calculating a viscosity of the solution as a function of the velocity measured, using technical processing means.

The process according to the invention can comprise a temperature stabilization of the channel, preferably at a temperature comprised between 36° C. and 38° C.

The solution is preferably a blood sample coming from a human or an animal.

The process according to the invention preferably does not comprise adding platelet and/or coagulation activator to the blood sample as taken.

DESCRIPTION OF THE FIGURES AND EMBODIMENTS

Other advantages and characteristics of the invention will become apparent on reading the detailed description of embodiments which are in no way limitative, and from the following attached drawings.

As these embodiments are in no way limitative, variants of the invention can in particular be considered, comprising only a selection of characteristics described or illustrated hereinafter, in isolation from the other characteristics described or illustrated (even if this selection is isolated within a phrase containing other characteristics), if this selection of characteristics is sufficient to confer a technical advantage or to differentiate the invention with respect to the state of the prior art. This selection comprises at least one, preferably functional, characteristic without structural details, and/or with only a part of the structural details if this part alone is sufficient to confer a technical advantage or to differentiate the invention with respect to the state of the prior art.

Firstly, a preferential embodiment of the process according to the invention will be described with reference to FIGS. 1 to 6.

Figure 1:
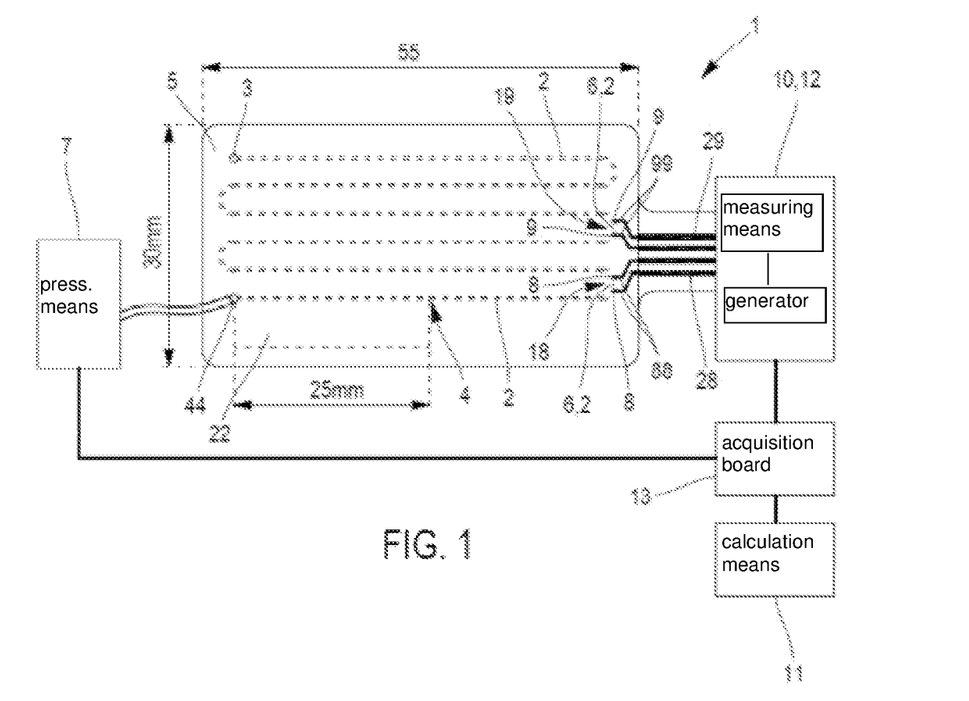
FIG. 1 is a diagrammatic view of device 1 used for implementing an embodiment of the process according to the invention, said device 1 comprising a cartridge 5 and measurement means 10.

The type of device 1 used for implementing the embodiment of the process according to the invention corresponds to the general type of device as described in the application WO2009/053841.

Figure 2:
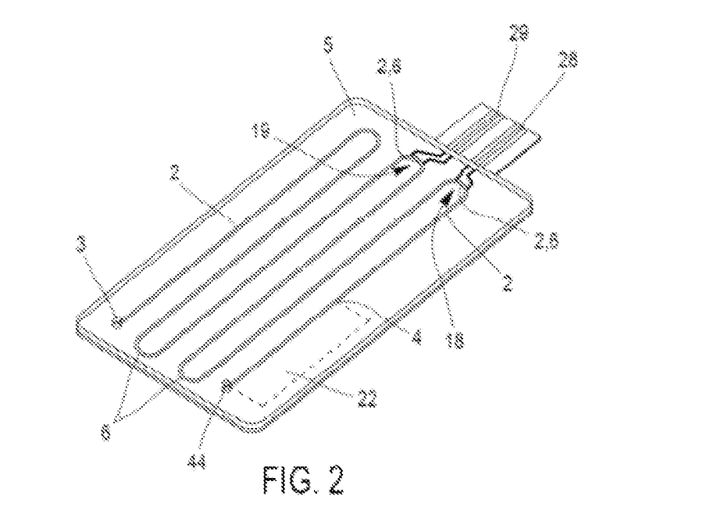
FIG. 2 is a perspective view of the cartridge 5 of the device 1, this cartridge 5 comprising a channel 2 provided for being filled with a solution.

This embodiment of the process according to the invention comprises producing, in a channel 2 of the device used 1, a primary vacuum (typically of approximately 5 kPa with respect to atmospheric pressure or to the pressure surrounding the device used).

This embodiment of the process according to the invention for characterizing a blood sample, comprises introducing into the channel 2 (still subjected to the primary vacuum), a solution comprising blood platelets (typically from 30 µl to 200 µl of solution) and coagulation factors.

The channel 2 comprises an inlet 3 (typically consisting of a bore 1 mm in diameter) and an outlet 4, the solution being introduced through the inlet 3 of the channel 2.

The outlet 4 of the channel opens into a reservoir 22, which serves for storing the blood solution so that the blood solution does not escape from the cartridge 5 for health and safety reasons.

The channel 2 is, more precisely, a capillary tube.

The solution is an undiluted whole blood solution comprising blood platelets.

The solution is a blood sample taken from a human or an animal, the process not comprising adding platelet activator (such as adenosine diphosphate (ADP), arachidonic acid, collagen, serotonin, thrombin, etc.) and/or coagulation activator (such as tissue factor, Factor XII, thrombin, etc.) to the blood sample as taken.

The channel 2 is made in a cartridge 5 (which can be monobloc or result from a superimposition of several plates), preferably in a plastic material (typically ethylene polyterephtalate, and/or polycarbonate.

For example, the cartridge 5 is an assembly of:
an upper plate made of transparent polycarbonate in order to monitor the circulation of the solution in the channel 2 and the reservoir 22 which are machined on one of the faces of this upper plate, and
a lower plate made of black XANTAR LDS 3730 PC, a polycarbonate containing copper particles that can be activated by laser in order to allow the electrolytic deposition of the electrodes described hereinafter, these two plates being hermetically sealed together (for example by a gasket, and/or by adhesive bonding and/or by laser welding etc.) in order to maintain the tightness of the channel 2 and to withstand pressures of 5 to 10 kPa.

The channel 2 as a length (between its inlet 3 and its outlet 4) of 260 mm.

The channel 2 is preferably serpentine-shaped with several loops 6, typically three to nineteen loops.

The channel 2 has an internal cross-sectional area which is constant from its inlet 3 to its outlet 4.

The channel 2 has a cross-sectional area which is constant from its inlet 3 to its outlet 4, typically square, rectangular or round or oval in shape. Its cross section has a diameter and/or a width and/or a height typically greater than 50 µm and/or less than 900 µm.

In this particular example, the channel 2 has a rectangular cross section 320 µm in height and 350 µm in width.

This embodiment of the process according to the invention also comprises creating a pressure difference between the inlet 3 and the outlet 4 of the channel 2, so as to move the solution forward from the inlet 3 towards the outlet 4 of the channel 2.

The pressure difference between the inlet 3 and the outlet 4 of the channel 2 is created by suction on the side with the outlet 4 of the channel 2.

The means 7 used for creating this pressure difference ensure a change in the velocity of the solution/gas front in the channel 2 by regulating the depression ΔP downstream at the outlet 4, the pressure upstream at the inlet 3 being atmospheric pressure. The means 7 comprise, for example, a vacuum pump (reference KNF NMP05M 6 VDC) and two solenoid valves (LFVA 50210H THE LEE CO, ESSEX). The limit pressure that can be provided by the system is approximately 70 kPa absolute (−30 kPa with respect to atmospheric pressure). The suction pressure is regulated to an accuracy of 0.5 kPa around the set-point pressure threshold fixed in order to have a differential pressure of 5 kPa with respect to atmospheric pressure on the day of the measurement.

The reservoir 22 is connected on one side to the outlet 4 and on another side to a passage 44 (which is typically a hole or channel) communicating with the means 7.

The device 1 optionally comprises means for detecting a "measure" detection means. These detection means comprise, for example, a photodiode, and are arranged in or oriented towards:
the outlet 4 of the channel 2, or
the reservoir 22, being closer to the outlet 4 than to the passage 44.

These "measurement" detection means are:

arranged in order to detect a defined fill level of the reservoir 22 with the blood solution and/or an arrival of the blood solution through the outlet 4 of the channel 2, and connected to means 10 for measuring an electrical signal, which means are triggered on detection of this defined fill level of the reservoir 22 with the blood solution (for example ⅕th filled) and/or an arrival of the blood solution through the outlet 4.

Thus, in the process according to the invention, the measurement (by the measurement means 10) of an electrical signal is triggered after (preferably just after) detection of this defined fill level of the reservoir 22 with the blood solution and/or an arrival of the blood solution through the outlet 4 of the channel 2.

The device 1 optionally comprises "stop" detection means. These detection means comprise, for example, a photodiode, and are arranged in or oriented towards:

the passage 44, or the reservoir 22, being closer to the passage 44 than to the outlet 4.

These "stop" detection means are:

arranged in order to detect a defined fill level of the reservoir 22 with the blood solution and/or an arrival of the blood solution through the passage 44, and connected to means (board 13) which control the means 7 used for creating the pressure difference, and which are arranged in order to stop the forward movement of the solution/gas front on detection of this defined fill level of the reservoir 22 with the blood solution (for example ⅘$^{th}$ filled) and/or an arrival of the blood solution through the passage 44.

Thus, in the process according to the invention, the forward movement of the solution/gas front in the channel 2 is stopped after (preferably just after) detection of this defined highest fill level of the reservoir 22 with the blood solution and/or an arrival of the blood solution through the passage 44.

The forward movement of the solution from the inlet 3 towards the outlet 4 of the channel 2 comprises a forward movement of a front between the solution extending from the front towards the inlet 3 of the channel 2 on the one hand, and a gas extending from the front towards the outlet 4 of the channel 2 on the other hand.

This front is called "front" or "solution/gas front" in the present description.

Thus, as the front is not a front between two different liquids, there is no risk of random diffusion of one liquid to another which could cause problems of reproducibility.

The gas is air. In other variants, the gas could be any gas, preferably:

a neutral gas among helium, neon, argon, krypton, xenon and radon or a mixture thereof and/or oxygen $O_2$, and/or nitrogen $N_2$, and/or hydrogen $H_2$, and/or carbon dioxide.

During the passage of the front through the inlet 3 of the channel 2, the solution has a shear rate at the internal walls of the channel 2 greater than 10,000 s$^{-1}$.

In the present description, all the shear rates $\gamma_w$ at the internal walls of the channel 2 are assumed to be calculated with the following formula:

$$\gamma_w = \frac{\Delta P}{2\mu L \sqrt{\frac{\pi}{S}}}$$

which is a Poiseuille-type approximation with a head loss coefficient, with $\Delta P$ the pressure difference $P_e - P_s$ between the pressure $P_e$ at the inlet 3 and the pressure $P_s$ at the outlet 4 of the channel 2, this difference (or at least the set-point of this difference imposed by the means 7) being constant (in order to imitate the blood circulation conditions in the cardiovascular system as closely as possible) and typically comprised between 5 and 10 kPa.

S the area of the internal cross section of the channel 2, whether this section is circular in a Poiseuille-type model or, as a first approximation, square or rectangular (preferably with the long sides of the rectangle less than twice as long as the short sides of the rectangle) or another shape, $\mu$ the dynamic viscosity of the solution (in Pa·s), theoretical or measured with a Couette viscometer L the length of the channel 2 between its inlet 3 and:

the solution/gas front if the solution has not yet reached the outlet 4, or the outlet 4 if the solution has reached the outlet 4

Figure 3:
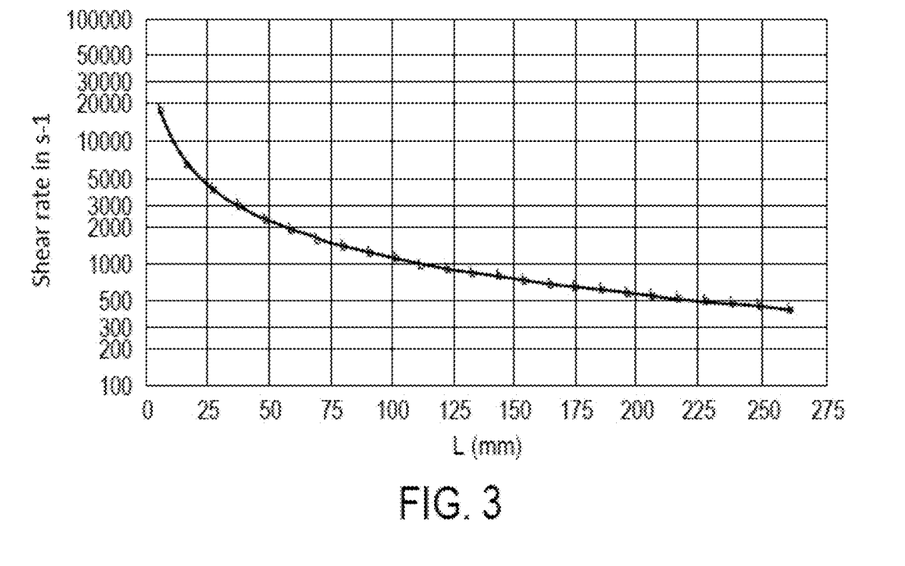
FIG. 3 illustrates the variation in the shear rate of the solution on the internal walls of the channel 2, as a function of the distance between the inlet 3 of the channel 2 and the solution/gas front.

FIG. 3 illustrates the variation in the shear rate of the solution at the internal walls of the channel 2, as a function of the distance between the inlet 3 of the channel 2 and the solution/gas front.

As illustrated in FIG. 3, during the forward movement of the solution from the inlet 3 towards the outlet 4 of the channel 2, the solution has a shear rate at the internal walls of the channel which decreases with time, more precisely during the forward movement of the front from the inlet 3 to the outlet 4, i.e. during a transitional state which precedes a steady state.

During the passage of the front through the outlet 4 of the channel 2, the solution has a shear rate at the internal walls of the channel less than 1,000 s$^{-1}$.

As a first approximation, at a given point in time (for a given position of the front in the channel 2), the shear rate of the solution at the internal walls of the channel 2 is constant from the inlet 3 of the channel 2 to the front, or up to the outlet 4 if the channel 2 is completely filled with the solution.

Thus, the invention gives access to high shear rates (greater than 10,000 s$^{-1}$, moderate stenosis), and to low shear rates (less than 1,000 s$^{-1}$, "normal" physiological value). The platelets are activated by the acceleration of the shear rates, but adhere in a deceleration zone and form stable aggregates where the shear has become physiological again. The invention thus makes it possible to imitate a range of conditions ranging from pathological conditions, where the decreasing shear gradient is the main activator of the platelets which adhere in order to form the thrombus, to physiological conditions for stabilizing the platelet aggregates. The invention makes it possible to stimulate the platelets with a temporal decreasing shear gradient without adding activators, and the measurement of the electrical signal on one (or each) pair 18, 19 of electrodes covered with platelet aggregates is carried out at physiological shears in order to have maximum reproducibility.

Figure 4:
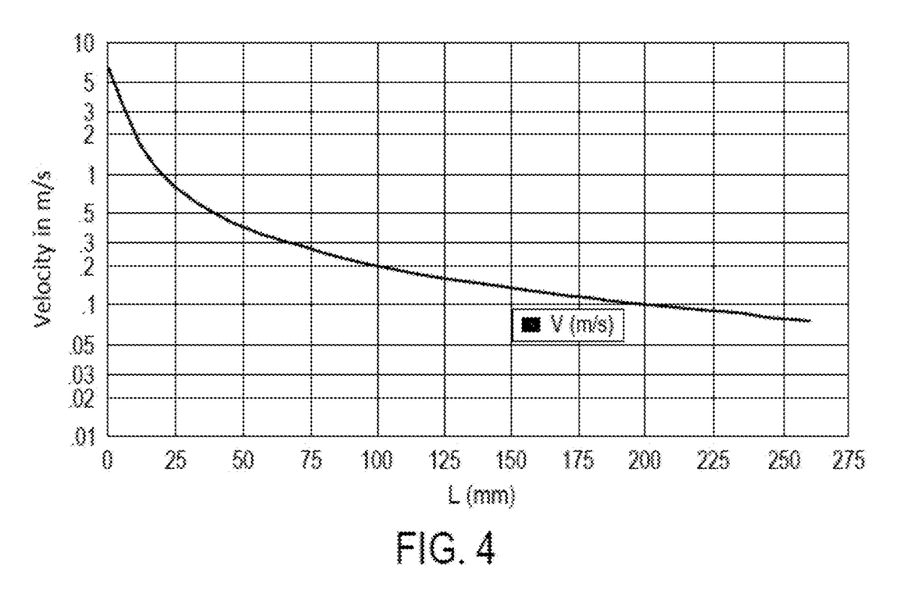
FIG. 4 illustrates the variation in the velocity of the solution/gas front, as a function of the distance between the inlet 3 of the channel 2 and the solution/gas front.

FIG. 4 illustrates the variation in the velocity of the solution/gas front, as a function of the distance between the inlet 3 of the channel 2 and the solution/gas front.

As illustrated in FIG. 4, the front has a forward movement velocity in the channel 2, which decreases with time during the forward movement of the solution in the channel 2, preferably until the solution reaches the outlet 4 of the channel 2, more precisely during the forward movement of the front from the inlet 3 to the outlet 4, i.e. during the transitional state. Thus, the invention gives access to a variation in the flow velocity. These conditions reflect the reduction in the flow velocity of the blood in the arterial circulation, from the aorta to the capillaries.

This embodiment of the process according to the invention comprises passing the solution into a measurement zone of the channel equipped with electrodes 8, 9 preferably with at least one pair 18 or 19 of electrodes, or even with several pairs of electrodes 18, 19.

Each pair 18 or 19 of electrodes is preferably situated at one of the loops 6 of the channel 2.

The electrodes 8, 9 have good oxidation resistance despite numerous passages of blood, dilute rinsing acids, physiological rinsing serum etc.

The electrodes 8, 9 (situated inside the channel 2), their respective electronic tracks 88, 99 and their respective connectors 28, 29 comprise, for example, platinum and/or gold, preferably an upper layer of platinum and/or gold in contact with the solution during the voltage measurement described below.

Each electrode 8, 9, each track 88, 99 and each connector 28. 29 is, for example, produced by successive deposition of three layers, with a width of 350 µm in the case of the electrodes, 300 µm in the case of the tracks and 800 µm in the case of the connectors:

5 µm to 8 µm thickness of copper, then
Possible doping with palladium (optional), then
2 µm to 5 µm thickness of nickel, then
0.05 to 0.1 µm thickness of gold.

The electrolytic deposition of the electrodes 8, 9, the electronic tracks 88, 99 and the connectors 28, 29 is carried out, for example, by the laser direct structuring technology (or LDS-LPKF), for example using an LPKF MicroLine 3D 160i laser driven by the LPKF MicroLine 3D Office Software. The metallization (copper, palladium, nickel, gold) is then carried out by successive chemical depositions.

Two electrodes, 8 or 9 respectively of the same pair, 18 or 19 respectively, are preferably spaced apart by from 100 µm to 4 mm, preferably between 300 µm and 1.5 mm, preferably approximately 1 mm.

This embodiment of the process according to the invention also comprises measurement, by said electrodes 8, 9 and the measurement means 10, of an electrical signal while said electrodes 8, 9 are covered with the solution in the channel 2.

The pressure difference between the inlet 3 and outlet 4 of the channel 2 (or at least the set-point of this pressure difference imposed by the means 7) is constant during the forward movement of the solution in the channel 2, preferably at least until the front reaches the outlet 4 of the channel 2 and/or up to the end of the measurement of the electrical signal by each pair 18 or 19 of electrodes.

The measurement of the electrical signal is carried out when:
the forward movement of the solution from the inlet 3 towards the outlet 4 of the channel 2 is in the steady state (average velocity of the solution and shear of the solution at the internal walls of the channel 2 being constant as a function of time, this steady state following the transitional state described above), and
the channel 2 is completely filled with the solution from the inlet 3 to the outlet 4 of the channel 2.

In fact, this steady state starts once the channel 2 is completely filled with the solution from the inlet 3 to the outlet 4.

In this steady state, the velocity of the solution varies spatially according to a velocity profile which is faster at the centre of the cross section of the channel 2 and slower on the internal walls of the channel 2, but this velocity profile is stable over time in the case of any point between the inlet 3 and the outlet 4.

The value of the Reynolds number (Re) at a cross section of the channel 2 can be calculated using the formula: Re=D.v.ρ/µ where:

D is the diameter of this cross section, which can be replaced in the preceding formula by $$2\sqrt{\frac{S}{\pi}}$$

or by the hydraulic diameter Dh (Dh=4*S/peri=4*width*height/(2*(width+height)) "peri" "width" and "height" being respectively the perimeter, the width and the height of this internal cross section of the channel, S being the area of this internal cross section of the channel 2, whether this cross section is circular in a Poiseuille-type model or, as a first approximation, square or rectangular (preferably with the long sides of the rectangle less than twice as long as the short sides of the rectangle) or another shape, v is the average velocity of the fluid flowing through this section ρ is the density of the fluid flowing through this section µ is the dynamic viscosity (theoretical or measured with a Couette viscometer) of the fluid flowing through this section For a pressure difference of 5 kPa, the Re values (typically comprised between 2 and 250 at 22° C. for a viscosity taken here at 0.0038 Pas) imitate those of the arterial system, from major trunks to arteries with small diameters, Starting from the inlet 3 of the channel 2 to the outlet 4 of the channel 2, the electrodes 8 of the second pair 18 are situated in a second half (preferably in the last third) of the channel 2; in other words, the electrodes 8 are situated between the middle of the length of the channel 2 and the outlet 4 of the channel 2 (preferably between the two thirds of the length of the channel 2 and the outlet 4 of the channel 2).

This embodiment of the process according to the invention also comprises, based on the measurement of the electrical signal, a calculation of an item of data relating to platelet discrimination and/or to coagulation by technical calculation means 11. This item of data is a quantified item of data, for example a real number on a scale from one to ten.

The calculation means 11 comprise only technical means, typically electronic means (analog and/or digital), a computer central processing unit, a processor and/or software means.

The measurement means 10 impose (by means of a current source 12) a constant electrical current between the electrodes 8, 9 of each pair 18, 19 and measure a voltage between the electrodes 8, 9 of each pair 18, 19.

The electrical current has a constant form as a function of time, typically a constant of 2 µA to 10 µA, preferably approximately 5 µA. The current remains constant during measurement of the voltage, which typically lasts less than 30 seconds, preferably less than 10 seconds, typically 5 seconds.

The resulting signal for each pair 18, 19 of electrodes is a non-linear variation of the voltage measured as a function of time.

The voltage measurement in the case of each pair 18, 19 of electrodes is synchronized with the electrical current imposed on this same pair 18, 19 of electrodes so as to measure the voltage when the intensity is constant.

Figure 5:
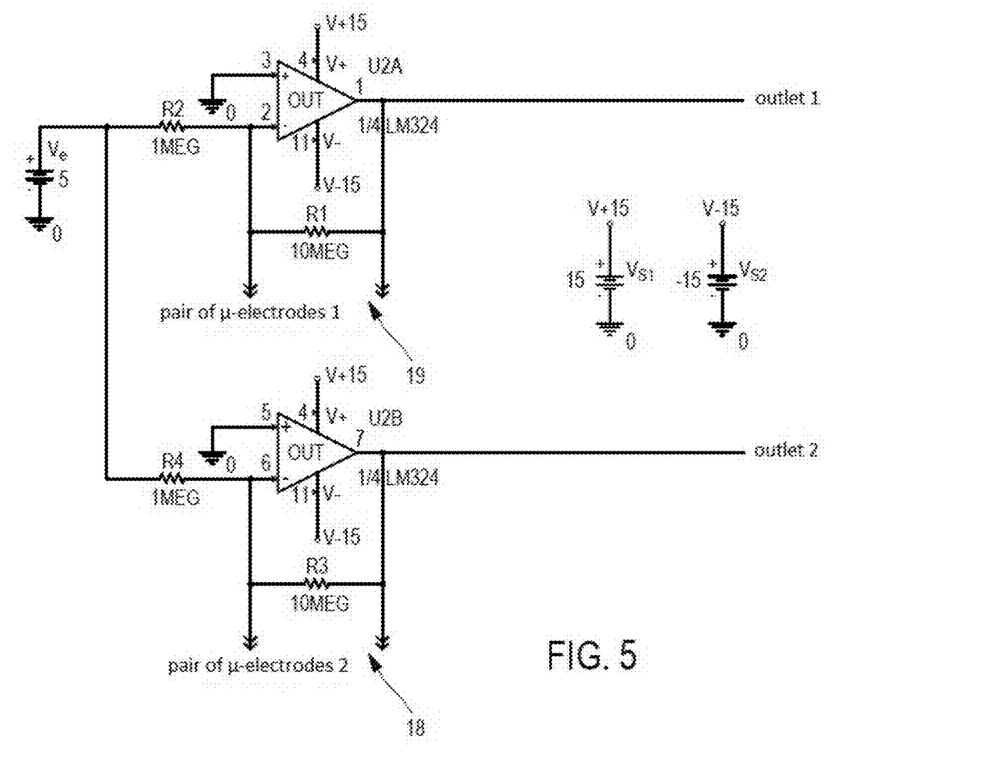
FIG. 5 is a diagram showing an electronic board of the measurement means 10.

The electronic diagram of part of the measurement means 10, illustrated in FIG. 5, shows a current source I, the amplitude and the form of which depend on the form of the inlet voltage $V_e$. Each pair 19, 18 is associated with an operational amplifier, the outlet voltage of which, $V_{S1}$ or $V_{S2}$ respectively, is equal to the difference in potential at the terminals of the pair of electrodes 9 or 8 respectively. Each outlet $V_{S1}$ or $V_{S2}$ of this board 10 is linked to an acquisition board 13.

The acquisition board 13 is, for example, a National Instruments board (reference "High-Speed M Series Multifunction DAQ for USB—16-Bit, up to 1.25 MS/s, Integrated BNC Connectivity") which comprises a 16-bit analog-digital converter (ADC) an eight-channel multiplexer (maximum sampling frequency 1.25 MHz) and two 16-bit digital-analog converters DAC) (2 MHz for two channels). In a more compact variant, the board 13 is replaced by a microcontroller.

The board 10, the generator 12 and the board 13 are programmed using calculation means 11 (computer) for example via Matlab or the open source Scilab software.

This embodiment of the process according to the invention comprises an integration, in time (typically over a few seconds, typically over 2 to 20 seconds preferably between t=3 s and t-5 s, t=0 s corresponding to the start of the imposition of constant current) of the voltage measured for each pair 18, 19 of electrodes.

This integration can be carried out directly by measurement means 10, or post-processing by the calculation means 11.

Figure 6:
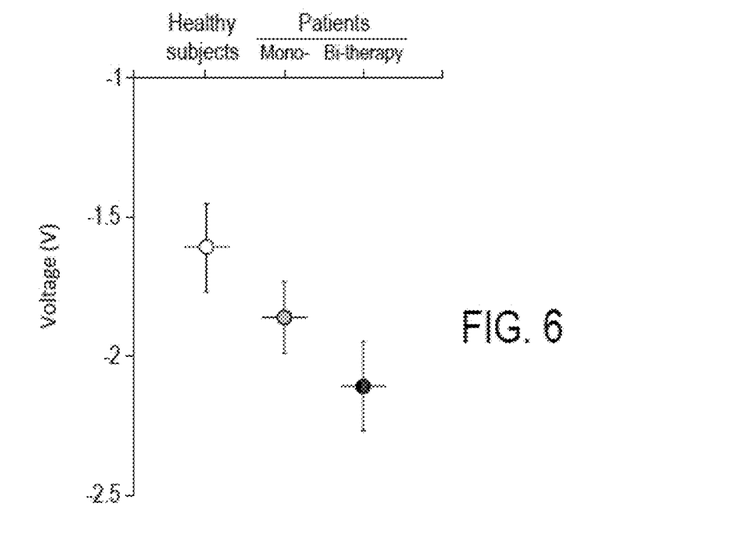
FIG. 6 illustrates different average values of the item of data relating to platelet discrimination (integration of the voltage signal) for different populations (healthy subjects, patients treated with platelet aggregation inhibiting monotherapies and patients treated with platelet aggregation inhibiting bi-therapies).

The value of this integration is directly proportional to the item of data relating to platelet discrimination in whole blood, which is an item of data the value of which makes it possible to discriminate between platelets functioning normally, i.e. very reactive to the shear stresses, and platelets not functioning normally, i.e. more weakly reactive to the shear stresses and makes it possible to discriminate between, for example:

patients treated with platelet aggregation inhibitors and healthy subjects and/or patients treated with aggregation-inhibiting monotherapies and those treated with aggregation-inhibiting bi-therapies, and/or patients treated with aggregation-inhibiting bi-therapies and those treated with aggregation-inhibiting tri-therapies, and/or patients treated with aggregation-inhibiting monotherapies and those treated with an aggregation-inhibiting monotherapy and a direct oral anticoagulant.

This is illustrated in FIG. 6, in an example where patients treated with monotherapies were treated with Prasugrel (Effient) or Clopidogrel (Plavix) and patients treated with bitherapies were treated with aspirin and Prasugrel (Effient) or aspirin and Clopidogrel (Plavix).

In this example, it was verified that the variation in value of this integration is not a measurement artefact or measurement noise but in fact corresponds to variations in platelet aggregation at the surface of electrodes. For this, the aggregation of platelets on the electrodes 8 was imaged using scanning electron microscopy (SEM). After measuring the voltage on the pair of electrodes 8, the plasma proteins and the non-adherent blood cells are removed by washing the channel 2 with a Tyrode-Hepes-BSA solution (135 mM NaCl, 4 mM KCl, 2 mM MgCl2, 0.9 mM NaH2PO4, 2.5 mM glucose, 2.5 mM pyruvate, 10 mM Hepes pH 7.35 and 0.35% bovine serum albumin (BSA)) for 1 minute. The two plates of the cartridge are separated, and the lower plate made of black Xantar 3730 LDS PC with the electrodes is immediately immersed in the fixative (0.1 M phosphate buffer and 2% glutaraldehyde). It is kept there at ambient temperature for two hours, then washed once with 0.2 M phosphate buffer. After fixing, this lower plate is kept in the phosphate buffer for a maximum of 24 hours. The biological material on this lower plate is dehydrated by being passed successively through baths of ethanol or acetone of increasing concentrations. The biological material on this lower plate is dried by desiccation with hexamethyldisylasane. The biological material on this lower plate is covered with a fine layer of gold (20-40 nm) by means of cathode sputtering (Scancoat Six, Edwards). The purpose of the metallization is to make the sample conductive of electrons, thus avoiding the accumulation of parasitic charges at its surface during the observation. For the observation, the portion of metallized plate is introduced into the enclosure under secondary vacuum of the SEM (Scanning Electron Microscope with tungsten filament, Stereoscan 260, Cambridge and digital acquisition system).

Imaging by scanning electron microscopy has made it possible to observe that the platelet aggregates rest on a fine film of fibrin at the surface of all the electrodes.

For the measurement, the microfluid cartridge 5 is connected (on the side with connectors 28, 29 respectively, connected to the electronic tracks 88, 99 respectively of the electrodes 8, 9 respectively):

to the source 12 of electrical current to the voltage measurement means 10 and to the calculation means 11.

The means 7 for creating the pressure difference between the inlet 3 and the outlet 4 of the channel 2 are also connected to the measurement means 10 and to the calculation means 11.

The acquisition board 13 is connected to the measurement means 10 and to the calculation means 11.

The morphological state of the fibrin depends on the quantity of thrombin and on the shear rates: fine films of fibrin at high rates and entangled fibre networks at low rates.

The invention thus makes it possible to integrate the platelet aggregation and the coagulation into the item of data calculated on the basis of the voltage measurement.

Thus, the invention also proves useful for monitoring patients suffering from atrial fibrillation treated with oral anticoagulants to prevent the risk of thromboembolism.

Imaging by scanning electron microscopy has made it possible to show a difference in the surface state between the electrodes 8, 9 and the "bare" walls of the channel 2.

By surface roughness is meant in the present description, parameters commonly denoted Ra, Rz and Rt in the technical field of roughness measurement (the numerical values of which correspond to a measurement using a Mahr Perthen PGK roughness measuring unit, with a calculation unit S4P; the measurements were carried out at 23° C. with an MFW probe head, a 250 probe arm and a probe length of 0.56 mm), for which Ra is the arithmetic mean of the variations (peaks and troughs of the height of the surface) at the mean surface height line, Rz is the maximum height defined as the distance between the line of the peaks and that of the troughs from the height of the surface, and Rt is the total height corresponding to the sum of the maximum peak and of the maximum trough from the height of the surface.

For the surface energy and/or hydrophobicity and/or wettability in the present description (measured at 23° C. via a GBX Digidrop Goniometer), the contact angle measurements (of a liquid drop on a solid surface in a gaseous environment) repeated for at least two liquids make it possible to obtain an equation system having the general form of the Owens-Wendt relationship:

$$\frac{\gamma_L \cdot (1 + \cos\theta_{SL})}{2 \cdot \sqrt{\gamma_L^D}} = \sqrt{\gamma_S^D} + \sqrt{\frac{\gamma_L^P}{\gamma_L^D}} \cdot \sqrt{\gamma_S^P}$$

Where:
$\theta_{SL}$ is the solid/liquid contact angle
$\gamma_L, \gamma_L^D, \gamma_L^P$ are, respectively, the total energy, the dispersive and polar component of the liquid considered
$\gamma_S^D, \gamma_S^P$ respectively the dispersive and polar component of the surface energy of the solid surface.

Drawing a straight line y=ax+b with y equal to the left-hand part of the preceding equation and x equal to $$\sqrt{\frac{\gamma_L^P}{\gamma_L^D}}$$

(for example with 3 points corresponding to deionized water, formamide and ethylene glycol), produces $a=(\gamma_S^P)^{1/2}$ and $b=(\gamma_S^d)^{1/2}$ i.e. a straight line the leading coefficient of which is the square root of the polar component of the surface energy and the intercept is the square root of the dispersive component of the surface energy. Finally, the total surface energy $\gamma_S$ (typically in mJ/m$^2$) is obtained by adding the polar component $\gamma_S^P$ and dispersive component $\gamma_S^D$ together.

Each electrode 8, 9 has a roughness Ra, Rt and/or Rz at least 10 times greater than the roughness Ra, Rt and/or Rz respectively, of the "bare" internal walls of the channel 2 (i.e. outside these electrodes 8, 9). Each electrode 8, 9 has a roughness Ra greater than 1 μm and/or less than 100 μm, and/or Rt greater than 5 μm and/or Rz greater than 7 μm (approaching that of the human arterial wall).

Such an arrangement of roughness seems to be at least partially responsible for an amplification of the platelet activation by a local increase in the shear. Locally, the shear rate is increased by a factor of three according to a calculation of finite elements with blood at 22° C. for a roughness Rz of 10 μm and a shear rate of 670 s−1 in the smooth duct which typically corresponds to a measurement electrode 8.

For the embodiment of FIGS. 1 to 6, roughness measurements carried out on the metallized Xantar LDS PC produce values of Ra, Rz and Rt equal to 1.91±0.36, 8.55±1.56 and 11.48±2.09 μm respectively (SD, n=12); in the case of the non-metallized Xantar LDS PC, Ra, Rz and Rt are 0.125±0.021, 0.695±0.007 and 1.030±0.099 μm respectively (n=2).

Each electrode 8, 9 is more hydrophobic than the "bare" internal walls of the channel 2 (i.e. outside these electrodes 8, 9). Each electrode 8, 9 has a total surface energy $\gamma_S$ at least twice the total surface energy $\gamma_S$ of the "bare" internal walls of the channel 2 (i.e. outside these electrodes 8, 9). Each electrode 8, 9 has a total surface energy $\gamma_S$ greater than 65 mJ/m$^2$ and/or the total surface energy $\gamma_S$ of the "bare" internal walls of the channel 2 (i.e. outside these electrodes 8, 9) is less than 40 mJ/m$^2$.

Such an arrangement seems to be at least partially responsible for an amplification of the coagulation.

For the embodiment of FIGS. 1 to 6, each electrode 8, 9 has a total surface energy $\gamma_S$ according to an experimental measurement on the copper/nickel/gold electrode 8, 9 zone equal to 76.78 mJ/m$^2$.

For the embodiment of FIGS. 1 to 6, the total surface energy $\gamma_S$ of the "bare" internal walls of the channel 2 according to an experimental measurement equals 25.75 mJ/m$^2$ on transparent PC and equals 32.99 mJ/m$^2$ on black PC.

Thus, in this embodiment:
the surface of the transparent PC of which the microchannel 2 is manufactured (machined or injection moulded) is very hydrophobic and will adsorb plasma proteins such as fibrinogen and activate the coagulation contact pathway. The low total surface energy with a polar component (at least 25% of the total surface energy) and the low roughness are, by contrast, rather unfavourable to platelet adhesion.
The non-metalized black PC is the least adhesive of the constituents of the channel 2 of the cartridge. The adsorption of the plasma proteins and the adhesion of the platelets to the bottom of the channel 2 with no electrode is therefore lowest at its surface.
The surface of the metallized PC is highly adhesive. The metal deposition has increased the surface energy by a factor greater than 2 and has considerably increased the hydrophobicity. The adsorption of the plasma proteins and the adhesion of the platelets is thus maximum at the surface of the electrodes 8, 9.

This embodiment of the process according to the invention also comprises a detection, preferably by photodiodes (preferably a pair of photodiodes, not shown) arranged laterally on the channel 2, of the passage of the front in the channel 2 (in front of the photodiodes) between the electrodes 8 and the outlet 4 of the channel 2.

The detection of the passage of the front by the photodiodes is sent to the measurement means 10 in order to ensure that the measurement means 10 will wait for the channel 2 to be completely filled and the reservoir 22 to be partially filled (1/10$^{th}$ for example) before measuring the electrical signal between the electrodes 8 and/or the electrodes 9.

This embodiment of the process according to the invention also comprises:
measuring, preferably by means of photodiodes (preferably a pair of photodiodes, not shown) arranged laterally on the channel 2 (preferably above or below the cartridge 1), a velocity of the solution (preferably of the front) in the channel 2 (in front of the photodiodes) between the electrodes 8 and the outlet 4 of the channel 2.
calculating, by technical processing means (for example by calculation means 11), a viscosity of the solution as a function of the velocity measured.

It is fairly difficult to measure a velocity with the photodiodes when the channel 2 is full.

Thus, the average velocity of the front between two points is measured, each point corresponding to a position of one of the photodiodes. The points are preferably situated close to the outlet 4 of the channel 2, where the variation in velocity of the front between these two points is small. With two photodiodes spaced apart by 2 to 10 mm, for example, the velocity under a constant and known AP is measured. This makes it possible to obtain the average viscosity of the solution with the Poiseuille formula.

Assessment of the blood viscosity is an additional criterion for assessing the benefit/risk of the antiplatelet bitherapies/tritherapies.

This embodiment of the process according to the invention comprises a temperature stabilization of the channel 2 and of the cartridge 5, preferably at a temperature comprised between 36° C. and 38° C., preferably between 36.5° C. et 37.5° C. This improves the reproducibility of the measurements, as the viscosity of the solution depends on the temperature. For this, the cartridge 5 in which the channel 2 is made is typically in contact with a thermostat (integrated in a support bearing the cartridge 1, with a heating resistor and/or a Peltier module), arranged to function for both cooling and heating.

Of course, the invention is not limited to the examples which have just been described and numerous adjustments can be made to these examples without exceeding the scope of the invention.

For example, in variants which can be combined together:
the number of pairs of electrodes 8, 9 as described above can be any number, each pair of electrodes preferably being situated at one of the loops 6 of the channel 2 (preferably a single pair of electrodes per loop); and/or
the process is implemented only with the electrodes 8:
  either in the device 1,
  or in a variant of the device 1 not comprising the electrodes 9; i.e. in an embodiment comprising only a single pair of electrodes 8 and/or
the measurement can be carried out with the electrodes 8 while the electrodes 9 are passive. Generally, there can be, between the inlet 3 and the measurement electrodes 8, one or more patches or deposits 9 (preferably of gold or platinum) in the channel 2, each patch or deposit 9 being arranged in order to be in contact with the blood solution filling the channel 2. Preferably:
  each pair of electrodes 8 and/or each (of the) patch(es) or deposit(s) 9 is preferably situated at one of the loops 6 of the channel 2 (preferably a single pair of electrodes 8 or patches or deposits 9 per loop); and/or
  each electrode 8, 9 and/or each patch or deposit 9 has a roughness Ra, Rt and/or Rz at least 10 times greater than the roughness Ra, Rt and/or Rz respectively of the "bare" internal walls of the channel 2 (i.e. outside these electrodes 8, 9 or patches or deposits 9). Such an arrangement of roughness seems to be at least partially responsible for an amplification of the platelet activation by a local increase in the shear.
  each electrode 8, 9 and/or each patch or deposit 9 has a roughness Ra greater than 1 μm and/or less than 100 μm, and/or Rt greater than 5 μm and/or Rz greater than 7 μm (approaching that of the human arterial wall). Such an arrangement of roughness seems to be at least partially responsible for an amplification of the platelet activation by a local increase in the shear.
  each electrode 8, 9 and/or each patch or deposit 9 is more hydrophobic than the "bare" internal walls of the channel 2 (i.e. outside these electrodes or patches or deposits 9). Such an arrangement seems to be at least partially responsible for an amplification of the coagulation.
  each electrode 8, 9 and/or each patch or deposit 9 has a total surface energy $\gamma_S$ at least twice the total surface energy $\gamma_S$ of the "bare" internal walls of the channel 2 (i.e. outside these electrodes or patches or deposits 9). Such an arrangement seems to be at least partially responsible for an amplification of the coagulation.
  each electrode 8, 9 and/or each patch or deposit 9 has a total surface energy rs greater than 65 mJ/m$^2$ and/or the total surface energy rs of the "bare" internal walls of the channel 2 (i.e. outside these electrodes or patches or deposits 9) is less than 40 mJ/m$^2$. Such an arrangement seems to be at least partially responsible for an amplification of the coagulation.

For example, a variant of the embodiment described above, with reference to the figures, would comprise the pair of electrodes 8, and at least five pairs of patches or deposits 9 of gold in the channel (resembling the pair of electrodes 9 but in a "passive" form, without track 99) upstream of the electrodes 8 (i.e. between the inlet 3 and the electrodes 8); and/or
  the suction pressure is regulated to an accuracy of less than 0.5 kPa around the set-point pressure threshold fixed in order to have a lower differential pressure than the embodiments described above (typically of 0.2 kPa) with respect to atmospheric pressure on the day of the measurement, making it possible to have lower shear rates (typically from 250 à 80 s$^{-1}$) at the electrodes, so as to promote the formation of a thrombus rich in fibrin and red blood cells, and thus not to be limited to monitoring the anti-platelet therapies. For a pressure difference ΔP of 0.2 kPa, the values of Re (typically comprised between 0.01 and 10 at 22° C.) approach those of the arterioles; and/or
  generally, the pressure difference ΔP is greater than 0.1 kPa (or even greater than 5 kPa) and/or less than 15 kPa (or even less than 10 kPa).

Of course, the various features, forms, variants and embodiments of the invention can be combined with one another in various combinations, provided that they are not incompatible or mutually exclusive. In particular, all the variants and embodiments described above can be combined together.

The invention claimed is:
1. Process for characterizing a blood sample, comprising:
introducing a solution comprising blood platelets into a channel (2), said channel comprising an inlet (3) and an outlet (4), the solution being introduced through the inlet of the channel,
creating a pressure difference between the inlet and the outlet of the channel, so as to move the solution forward from the inlet towards the outlet of the channel,
passing the solution into a measurement zone of the channel equipped with electrodes (8),
measuring an electrical signal using measurement means (10) and said electrodes, while said electrodes are covered with the solution in the channel,
wherein the forward movement of the solution from the inlet towards the outlet of the channel comprises a forward movement of a front between
the solution extending from the front towards the inlet of the channel, and
a gas extending from the front towards the outlet of the channel.

2. Process according to claim 1, wherein, during the passage of the front through the inlet of the channel, the solution has a shear rate at the internal walls of the channel greater than 10,000 s$^{-1}$.

3. Process according to claim 1, wherein, during the forward movement of the front from the inlet towards the outlet of the channel, the solution has a shear rate at the internal walls of the channel which decreases with time.

4. Process according to claim 1, wherein during the passage of the front through the outlet of the channel, the solution has a shear rate at the internal walls of the channel less than 1000 s$^{-1}$.

5. Process according to claim 1, wherein the pressure difference between the inlet and the outlet of the channel is constant during the forward movement of the solution in the channel.

6. Process according to claim 1, wherein the channel has a cross-sectional area that is constant from inlet to outlet of the channel.

7. Process according to claim 1, wherein the pressure difference between the inlet and the outlet of the channel is created by suction on the side with the outlet of the channel.

8. Process according to claim 1, wherein the front has a forward movement velocity in the channel which decreases with time during the forward movement of the solution in the channel.

9. Process according to claim 1, wherein the gas is air.

10. Process according to claim 1, wherein the measurement of the electrical signal is carried out when the progression of the solution from the inlet towards the outlet of the channel is in a steady state, said channel being filled with the solution from the inlet to the outlet of the channel.

11. Process according to claim 1, wherein the electrodes (8) are situated in a second half of the channel starting from the inlet of the channel.

12. Process according to claim 1, further comprising, based on the measurement of the electrical signal, a calculation of an item of data relating to platelet discrimination.

13. Process according to claim 1, wherein the measurement means impose a constant electrical current between the electrodes and measure a voltage between the electrodes while the electrical current is imposed.

14. Process according to claim 13, further comprising an integration, over time, of the voltage measured.

15. Process according to claim 1, further comprising:
   detecting the passage of the front between the electrodes and the outlet of the channel, and/or
   measuring a velocity of the solution in the channel, and calculating a viscosity of the solution as a function of the velocity measured, using technical processing means.

16. Process according to claim 1, further comprising a temperature stabilization of the channel.

17. Process according to claim 1, wherein the solution is a blood sample coming from a human or an animal, the process not comprising an addition of platelet activator to the blood sample as taken.

18. Process according to claim 1, wherein, during the forward movement of the front from the inlet towards the outlet of the channel, the solution has a shear rate at the internal walls of the channel which decreases with time, until the front reaches the outlet of the channel.

19. Process according to claim 1, wherein the pressure difference between the inlet and the outlet of the channel is constant during the forward movement of the solution in the channel, at least until the front reaches the outlet of the channel and/or up to the measurement.

20. Process according to claim 1, wherein the front has a forward movement velocity in the channel which decreases with time during the forward movement of the solution in the channel, until the front reaches the outlet of the channel.

* * * * *